United States Patent
Collins et al.

(10) Patent No.: US 7,427,621 B2
(45) Date of Patent: *Sep. 23, 2008

(54) CYCLIC SULFAMIDES FOR INHIBITION OF GAMMA-SECRETASE

(75) Inventors: Ian James Collins, Redhill (GB); Joanne Clare Hannam, Bishops Stortford (GB); Timothy Harrison, Great Dunmow (GB); Andrew Madin, Sawbridgeworth (GB); Mark Peter Ridgill, Watton-at-Stone (GB)

(73) Assignee: Merck Sharp & Dohme Limited, Hoddesdon, Hertfordshire (GB)

( * ) Notice: Subject to any disclaimer, the term of this patent is extended or adjusted under 35 U.S.C. 154(b) by 475 days.

This patent is subject to a terminal disclaimer.

(21) Appl. No.: 10/533,272

(22) PCT Filed: Oct. 31, 2003

(86) PCT No.: PCT/GB03/04728

§ 371 (c)(1), (2), (4) Date: Apr. 28, 2005

(87) PCT Pub. No.: WO2004/039800

PCT Pub. Date: May 13, 2004

(65) Prior Publication Data

US 2006/0135570 A1 Jun. 22, 2006

(30) Foreign Application Priority Data

Nov. 1, 2002 (GB) .................................. 0225475.3

(51) Int. Cl.
- *A61K 31/433* (2006.01)
- *A61P 25/28* (2006.01)
- *C07D 285/14* (2006.01)

(52) U.S. Cl. .................. 514/255.05; 514/278; 514/362; 546/16; 548/126

(58) Field of Classification Search .................. 514/362, 514/255.05, 278; 546/16; 548/126
See application file for complete search history.

(56) References Cited

U.S. PATENT DOCUMENTS

| 5,703,129 A | 12/1997 | Felsenstein et al. |
| 6,310,107 B1 | 10/2001 | Kato et al. |
| 7,041,689 B2 * | 5/2006 | Collins et al. ............... 514/362 |
| 7,138,400 B2 * | 11/2006 | Collins et al. ............. 514/234.2 |
| 7,282,513 B2 * | 10/2007 | Collins et al. ............... 514/362 |

FOREIGN PATENT DOCUMENTS

| WO | WO 01/70677 | 9/2001 |
| WO | WO 02/36555 | 5/2002 |

OTHER PUBLICATIONS

Patini et al, Chem Rev. 1996, 96, 3147-3176.*
G. Rishton et al.,m "Fenchylamine Sulfonamide Inhibitors of Amyloid Beta Peptide Production by the Gamma-Secretase Proteolytic Pathway: Potential Small-Molecule Therapeutic Agents for the Treatment of Alzheimer's Disease", J. Med Chem., vol. 43, pp. 2297-2299 (2000).

* cited by examiner

*Primary Examiner*—Rei-tsang Shiao
*Assistant Examiner*—Susannah Chung
(74) *Attorney, Agent, or Firm*—William Krovatin; Raynard Yuro

(57) ABSTRACT

Compounds of formula I:

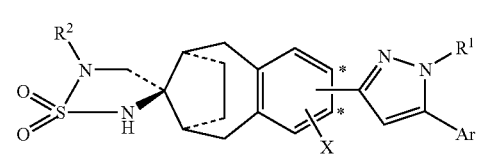

inhibit the processing of AP by gamma-secretase, and hence are useful for treatment or prevention of Alzheimer's disease.

8 Claims, No Drawings

CYCLIC SULFAMIDES FOR INHIBITION OF GAMMA-SECRETASE

CROSS REFERENCE TO RELATED APPLICATIONS

This application is a U.S. National Phase application under 35 U.S.C. § 371 of PCT Application No. PCT/GB03/004728, filed Oct. 31, 2003, which claims priority under 35 U.S.C. § 119 from GB Application No. 0225475.3, filed Nov. 1, 2002.

The present invention relates to a novel class of compounds, their salts, pharmaceutical compositions comprising them, processes for making them and their use in therapy of the human body. In particular, the invention relates to novel sulfamide derivatives which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There are relatively few reports in the literature of compounds with inhibitory activity towards γ-secretase, as measured in cell-based assays. These are reviewed in WO 01/70677. Many of the relevant compounds are peptides or peptide derivatives.

WO 01/70677 and WO 02/36555 disclose, respectively, sulfonamido- and sulfamido-substituted bridged bicycloalkyl derivatives which are believed to be useful in the treatment of Alzheimer's disease, but do not disclose or suggest compounds in accordance with the present invention.

The present invention provides a novel class of bridged bicycloalkyl sulfamide derivatives which show a particularly strong inhibition of the processing of APP by the putative γ-secretase, and thus are useful in the treatment or prevention of AD.

According to the invention there is provided a compound of formula I:

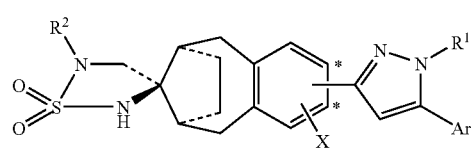

wherein the pyrazole group is attached at one of the positions indicated by an asterisk and X is attached at a position adjacent thereto;

X represents H, OH, $C_{1-4}$alkoxy, Cl or F;

Ar represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy;

$R^1$ represents a hydrocarbon group of 1-5 carbon atoms which is optionally substituted with up to 3 halogen atoms; and $R^2$ represents H or a hydrocarbon group of 1-10 carbon atoms which is optionally substituted with up to 7 halogen atoms;

provided that when X is H, $R^2$ does not represent 2,2,2-trifluoroethyl; or a pharmaceutically acceptable salt thereof.

In a subset of the compounds of formula I, $R^2$ represents H or a hydrocarbon group of 1-10 carbon atoms which is optionally substituted with up to 3 halogen atoms.

It will be readily apparent to those skilled in the art that any compound in accordance with formula I may exist in two enantiomeric forms, depending on which of the ring positions indicated by an asterisk is bonded to the pyrazole ring. Formula I thus encompasses enantiomers of formulae IIa and IIb:

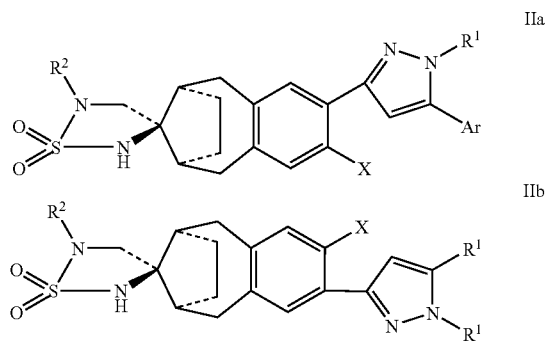

wherein X, Ar, $R^1$ and $R^2$ are as defined previously, and also enantiomers of formulae IIIa and IIIb:

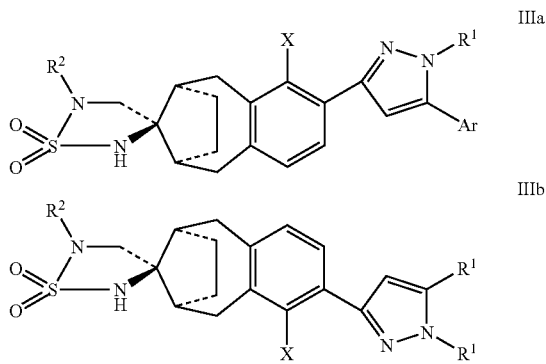

wherein X, Ar, $R^1$ and $R^2$ are as defined previously.

It will also be apparent that when X represents H formula IIa is identical to formula IIIa and formula IIb is identical to formula IIIb.

It is to be emphasised that the invention, for each compound in accordance with formula I, encompasses both enantiomeric forms, either as homochiral compounds or as mixtures of enantiomers in any proportion.

In a preferred embodiment of the invention, the compound of formula I is a homochiral compound of formula IIa or formula IIIa, or a pharmaceutically acceptable salt thereof.

Where a variable occurs more than once in formula I or in a substituent thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The expression "$C_{3-6}$cycloalkyl" as used herein refers to nonaromatic monocyclic hydrocarbon ring systems comprising from 3 to 6 ring atoms. Examples include cyclopropyl, cyclobutyl, cyclopentyl; cyclohexyl and cyclohexenyl.

The expression "cycloalkylalkyl" as used herein includes groups such as cyclopropylmethyl, cyclobutylmethyl, cyclopentylmethyl and cyclohexylmethyl.

The term "halogen" as used herein includes fluorine, chlorine, bromine and iodine, of which fluorine and chlorine are preferred.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, benzenesulfonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, X preferably represents H, OH or F, more preferably H or F. In one particular embodiment, X is H. In another particular embodiment, X is F.

Ar represents phenyl or 6-membered heteroaryl, either of which bears 0-3 substituents independently selected from halogen, $CF_3$, $CHF_2$, $CH_2F$, $NO_2$, $CN$, $OCF_3$, $C_{1-6}$alkyl and $C_{1-6}$-alkoxy. Examples of suitable 6-membered heteroaryl groups represented by Ar include pyridyl, pyrazinyl, pyrimidinyl, pyridazinyl and triazinyl, of which pyridyl is a preferred example. Preferably, the phenyl or heteroaryl ring bears 0 to 2 substituents. Preferred substituents include halogen (especially chlorine and fluorine), CN, $C_{1-6}$alkyl (especially methyl), $C_{1-6}$alkoxy (especially methoxy), $OCF_3$ and $CF_3$. If two or more substituents are present, preferably not more than one of them is other than halogen or alkyl. Examples of groups represented by Ar include phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Suitable specific values for Ar include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 3,4,5-trifluorophenyl, 4-cyanophenyl, 4-methylphenyl, 4-methoxyphenyl, 2-(trifluoromethyl)phenyl, 4-(trifluoromethyl)phenyl, 4-(trifluoromethoxy)phenyl, pyridin-2-yl, pyridin-3-yl, pyridin-4-yl, pyrazin-2-yl, 5-methylpyridin-2-yl, 5-fluoropyridin-2-yl, 5-chloropyridin-2-yl, 5-(trifluoromethyl)pyridin-2-yl and 6-(trifluoromethyl)pyridin-3-yl. Preferred examples include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 4-(trifluoromethyl)phenyl, pyridin-2-yl, pyridin-3-yl and pyridin-4-yl.

In a particularly preferred embodiment, Ar represents 4-fluorophenyl.

$R^1$ represents a hydrocarbon group of 1-5 carbon atoms which is optionally substituted with up to 3 halogen atoms, and thus may comprise cyclic or acyclic hydrocarbon residues or combinations thereof, saturated or unsaturated, up to a maximum of 5 carbon atoms in total. The hydrocarbon group represented by $R^1$ is preferably unsubstituted or is substituted with up to 3 fluorine atoms Examples include methyl, ethyl, n-propyl, isopropyl, n-butyl, sec-butyl, t-butyl, fluoromethyl, difluoromethyl, trifluoromethyl, 2,2,2-trifluoroethyl, cyclopropyl, cyclopropylmethyl and allyl. Preferred examples include methyl, ethyl and 2,2,2-trifluoroethyl. Most preferably, $R^1$ represents methyl.

$R^2$ represents H or a hydrocarbon group of 1-10 carbon atoms which is optionally substituted with up to 7 halogen atoms, with the proviso that when X is H, $R^2$ does not represent 2,2,2-trifluoroethyl. Suitable hydrocarbon groups represented by $R^2$ include alkyl, cycloalkyl, cycloalkylalkyl, alkenyl and benzyl groups optionally bearing up to 7, preferably up to 5, and most preferably up to 3 halogen substituents, the preferred halogen substituent being fluorine or chlorine, especially fluorine. Said alkyl, cycloalkyl, cycloalkylalkyl and alkenyl groups typically comprise up to 6 carbon atoms. Examples of groups represented by $R^2$ include H, benzyl, n-propyl, 2,2-dimethylpropyl, n-butyl, isopropyl, t-butyl, 2,2,2-trifluoroethyl, 2,2-difluoroethyl, 2,2,3,3,3-pentafluoropropyl, 3,3,3-trifluoropropyl, allyl, cyclopropyl, cyclobutyl and cyclopropylmethyl.

Examples of compounds in accordance with the invention include compounds of formula IIa or formula IIIa in which Ar is 4-fluorophenyl, $R^1$ is methyl and X and $R^2$ are as indicated in the following table:

| Formula (IIa or IIIa) | X | $R^2$ |
|---|---|---|
| IIa | F | 2,2,2-trifluoroethyl |
| IIIa | F | 2,2,2-trifluoroethyl |
| IIa | OH | 2,2,2-trifluoroethyl |
| * | H | allyl |
| * | H | n-propyl |
| * | H | 2,2-dimethylpropyl |
| * | H | cyclobutyl |
| * | H | benzyl |

-continued

| Formula (IIa or IIIa) | X | $R^2$ |
|---|---|---|
| * | H | n-butyl |
| * | H | cyclopropylmethyl |
| * | H | 3,3,3-trifluoropropyl |
| * | H | isopropyl |
| * | H | t-butyl |
| * | H | cyclopropyl |
| * | H | 2,2,3,3,3-pentafluoropropyl |
| * | H | 2,2-difluoroethyl |

* - when X is H, formulae IIa and IIIa are identical.

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's Disease, a suitable dosage level is about 0.01 to 250 mg/kg per day, preferably about 0.01 to 100 mg/kg per day, more preferably about 0.05 to 50 mg/kg of body weight per day, and for the most preferred compounds, about 0.1 to 10 mg/kg of body weight per day. The compounds may be administered on a regimen of 1 to 4 times per day. In some cases, however, a dosage outside these limits may be used.

Compounds of formula I in which $R^2$ is other than H may be prepared by reaction of an aziridine derivative (1) with $R^{2a}NH_2$:

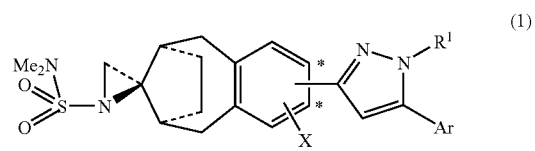

(1)

wherein the pyrazole group is attached at one of the positions indicated by an asterisk and X is attached at a position adjacent thereto, $R^{2a}$ is $R^2$ that is other than H, and X, Ar, $R^1$ and $R^2$ have the same meanings as before. The reaction may be carried out by heating the reagents at 100° C. in DMSO in a sealed tube for 16 hours.

Corresponding compounds wherein $R^2$ is H may be prepared by reacting an aziridine (1) with p-methoxybenzylamine in the manner described above, and treating the product with trifluoroacetic acid at ambient temperature to remove the p-methoxybenzyl group.

The aziridines (1) may be prepared by reaction of imines (2) with trimethylsulfoxonium iodide in the presence of sodium hydride:

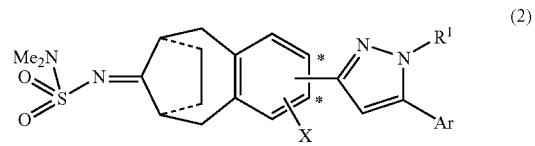

(2)

where X, Ar and $R^1$ have the same meanings as before. The reaction takes place in DMSO at ambient temperature.

The imines (2) may be prepared by condensation of ketones (3) with $Me_2NSO_2NH_2$:

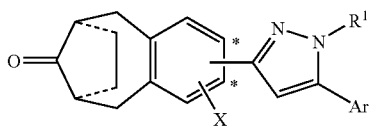
(3)

where X, Ar and $R^1$ have the same meanings as before. The reaction may be carried out by refluxing the reagents in THF in the presence of titanium (IV) ethoxide for 16 hours.

The ketones (3) may be prepared by coupling of boronates (4) with pyrazole derivatives (5):

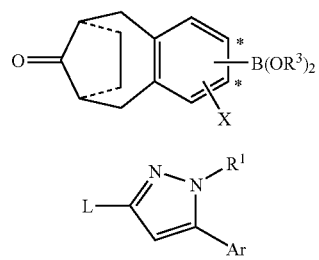
(4)

(5)

wherein $R^3$ represents H or $C_{1-6}$alkyl, or the two $OR^3$ groups complete a cyclic boronate ester such as the pinacolate, L represents a leaving group such as triflate, bromide or iodide (preferably triflate), and X, Ar and $R^1$ have the same meanings as before. The coupling takes place in the presence of a Pd catalyst such as tetrakis(triphenylphosphine)palladium(0), typically in the presence of an inorganic base such as potassium acetate or potassium carbonate in DMF at 100° C.

Boronates (4) may be prepared by reaction of triflates (6) with a suitable boron reagent, such as bis(pinacolato)diboron:

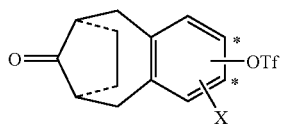
(6)

wherein Tf represents trifluoromethanesulfonyl and X has the same meaning as before. The reaction takes place under similar conditions as the coupling of (4) and (5), although the preferred catalyst is [1,1'-bis(diphenylphosphino)ferrocene] dichloropalladium(II).

Triflates (6) are prepared from phenols (7) by reaction with triflic anhydride:

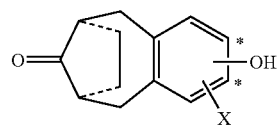
(7)

where and X has the same meaning as before. The reaction takes place in dichloromethane solution at 0° C. in the presence of a base such as pyridine.

The phenols (7) in which X is H are known in the literature (*J. Org, Chem.* 1982, 47, 4329), and the other compounds of formula (7) may be prepared analogously, or by suitable manipulation (e.g. halogenation) of (7) (X=H).

Pyrazoles (5) in which L is triflate are accessible from the reaction of alkynes Ar—C≡C—$CO_2$Me with $R^1NHNH_2$ and treatment of the resulting pyrazolones with triflic anhydride. Pyrazoles (5) in which L is Br are available by reaction of nonaflates (8) with ArZnBr:

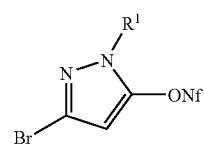
(8)

where Nf represents nonafluorobutanesulfonyl, and Ar and $R^1$ have the same meaning as before.

In an alternative route to the compounds of formula I, triflates (9a) are coupled with pyrazole stannanes (10):

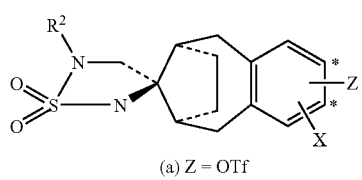
(9)

(a) Z = OTf
(b) Z = $B(OR^3)_2$ (10)

where X, Ar, $R^1$, $R^2$, $R^3$ and Tf have the same meanings as before. The coupling takes place in the presence of a Pd catalyst such as tetrakis(triphenylphosphine)palladium(0), in the presence lithium chloride in dioxan at 100° C.

Triflates (9a) may be prepared by conversion of the ketone group of (7) to a cyclic sulfamide moiety by the process described above, and treatment of the phenolic product with triflic anhydride. Stannane derivatives (10) may be prepared as described for Intermediate D in the Examples herein.

Alternatively, triflates (9a) may be converted to boronates (9b) and coupled with pyrazoles (5).

The phenol precursors of triflates (9a) in which X is H are amenable to chemical manipulation (e.g. fluorination) to provide corresponding compounds in which X is other than H. Alternatively, said phenols may be iodinated to provide the corresponding ortho-iodophenols, which may be transformed into boronates (9b) (X=OH) and coupled with pyrazoles (5) to provide compounds of formula I in which X is OH.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

In a preferred route to enantiomerically pure compounds of formula I, racemic intermediates (7) are subjected to preparative chiral HPLC to provide the corresponding homochiral intermediates, which are then converted to homochiral compounds of formula I by the routes indicated above.

Where they are not commercially available, the starting materials and reagents used in the above-described synthetic schemes may be prepared by conventional means.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups maybe removed at a convenient subsequent stage using methods known from the art.

An assay which can be used to determine the level of activity of compounds of the present invention is described in WO01/70677. A preferred assay to determine such activity is as follows:
1) SH-SY5Y cells stably overexpressing the βAPP C-terminal fragment SPA4CT, are cultured at 50-70% confluency. 10 mM sodium butyrate is added 4 hours prior to plating.
2) Cells are plated in 96-well plates at 35,000 cells/well/100 μL in Dulbeccos minimal essential medium (DMEM) (phenol red-free)+10% foetal bovine serum (FBS), 50 mM HEPES buffer (pH 7.3), 1% glutamine.
3) Make dilutions of the compound plate. Dilute stock solution 18.2× to 5.5% DMSO and 11× final compound concentration. Mix compounds vigorously and store at 4° C. until use.
4) Add 10 μL compound/well, gently mix and leave for 18 h at 37° C., 5% $CO_2$.
5) Prepare reagents necessary to determine amyloid peptide levels, for example by Homogeneous Time Resolved Fluorescence (HTRF) assay.
6) Plate 160 μL aliquots of HTRF reagent mixture to each well of a black 96-well HTRF plate.
7) Transfer 40 μL conditioned supernatant from cell plate to HTRF plate. Mix and store at 4° C. for 18 hours.
8) To determine if compounds are cytotoxic following compound administration, cell viability is assessed by the use of redox dye reduction. A typical example is a combination of redox dye MTS (Promega) and the electron coupling reagent PES. This mixture is made up according to the manufacturer's instructions and left at room temperature.
9) Add 10 μL/well MTS/PES solution to the cells; mix and leave at 37° C.
10) Read plate when the absorbance values are approximately 0.4-0.8. (Mix briefly before reading to disperse the reduced formazan product). 11) Quantitate amyloid beta 40 peptide using an HTRF plate reader.

Alternative assays are described in *Biochemistry*, 2000, 39(30), 8698-8704.

See also, *J. Neuroscience Methods*, 2000, 102, 61-68.

The compounds of the present invention show unexpectedly high affinities as measured by the above assays. Thus the following Examples all had an $ED_{50}$ of less than 100 nM, typically less than 10 nM, and frequently less than 1 nM in at least one of the above assays. In general, the compounds also exhibit good oral bioavailability and/or brain penetration.

The following examples illustrate the present invention.

EXAMPLES

Intermediate A

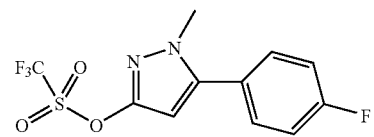

To a solution of methyl 4-(fluorophenyl)propynoate (*J. Org. Chem.* 1987, 52(16), 3662-8) (13 g, 73 mmol) in methanol (60 ml) was added water (60 ml) followed by methylhydrazine (4 ml, 77 mmol), the mixture was stirred for 6 hrs at 60° C. then left to stand overnight. The solid was filtered and washed with water then a minimum volume of methanol and dried overnight, affording 7.7 g of 5-(4-fluorophenyl)-1-methyl-1,2-dihydropyrazol-3-one (55%). δ ($^1$H, 500 MHz, $CDCl_3$) 3.68 (3H, s), 5.68 (1H, s), 7.13-7.17 (2H, m), 7.37-7.40 (2H, m).

To a cooled suspension of the above pyrazolone (15.5 g, 81 mmol) in dry pyridine (100 ml) was added in three portions trifluoromethanesulfonic anhydride (24 g, 85 mmol) maintaining the temperature below 5° C. The cooling bath was then removed and the reaction was stirred for two hours before pouring into 2M hydrochloric acid and extracting into ethyl acetate. The organic layer was washed with brine, saturated sodium hydrogen carbonate, and dried (sodium sulfate), filtered and evaporated to yield a residue which was dissolved in toluene and evaporated and then dissolved in isohexane and filtered through a plug of silica, eluting with dichloromethane. The solvent was evaporated to yield product as a colourless oil (23.4 g, 89%) δ ($^1$H, 500 MHz, $CDCl_3$) 3.80 (3H, s), 6.14 (1H, s), 7.15-7.19 (2H, m), 7.38-7.42 (2H, m).

Intermediate B

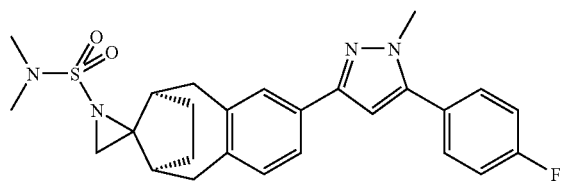

Step 1

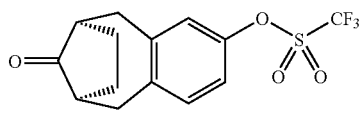

Racemic 2-hydroxy-5,6,7,8,9,10-hexahydro-6,9-methanobenzo[α][8]annulen-11-one (*J. Org. Chem*, 1982, 47, 4329) was resolved using a Berger SFC semi-preparative instrument (chiralpak AS (25×2 cm, 20 um); 15% MeOH/CO$_2$@50 mL/min; 35° C.; 100 bar), retaining the second eluted enantiomer.

To a stirred solution of the homochiral phenol (6.83 g, 34 mmol) in dry DCM (40 mL) at 0° C. under nitrogen was added pyridine (3.8 mL, 47 mmol) followed by triflic anhydride (8.0 mL, 47 mmol). The reaction was stirred at 0° C. for 2 hours, water (40 mL) added, the layers separated, and the aqueous layer extracted with DCM (×2). The combined extracts were washed with brine (×1), dried (MgSO$_4$), filtered and evaporated. The residue was purified by chromatography on silica, eluting with 10-15% EtOAc/hexane, to give the triflate (9.64 g, 85%). (400 MHz $^1$H, δ-CDCl$_3$) 1.28 (2H, m), 1.92 (2H, m), 2.64 (2H, m), 2.85-3.05 (4H, m), 7.13 (2H, m), 7.29 (1h, m).

Step 2

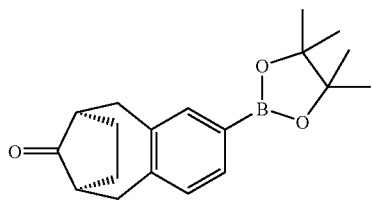

A solution of the triflate from Step 1 (9.64 g, 29 mmol), 1,1'-bis(diphenylphosphino)ferrocene (1.60 g, 2.8 mmol), bis(pinacolato)diboron (8.05 g, 32 mmol) and KOAc (8.49 g, 86 mmol) in dry DMF (200 mL) was deoxygenated by bubbling nitrogen through the solution for 20 minutes. [1,1'-Bis(diphenylphosphino)ferrocene]palladium (II) chloride (2.354 g, 2.9 mmol) was added and deoxygenation was continued for a further 10 minutes. The reaction was heated at 100° C. for 4 hours, then allowed to cool and diluted with water (400 mL). The catalyst was removed by filtration through Hyflo® and the filtrate was extracted with EtOAc (×3). The combined extracts were washed with water then brine, dried (MgSO$_4$), filtered and evaporated. The residue was purified by chromatography on silica, eluting with 10-20% EtOAc/hexane to give the product (7.39 g, 82%). (360 MHz $^1$H, δ-CDCl$_3$) 1.29 (2H, m), 1.35 (12H, s), 1.85 (2H, m), 2.59 (2H, m), 2.84-3.01 (4H, m), 7.21 (1H, m), 7.63 (2H, m).

Step 3

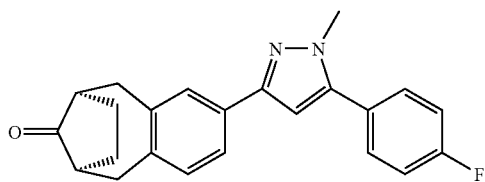

A solution of the boronate from Step 2 (2.06 g, 6.6 mmol), Intermediate A (1.95 g, 6.0 mmol), and sodium carbonate (0.70 g, 6.6 mmol) in dry DMF (30 mL) was deoxygenated by bubbling nitrogen through the solution for 30 minutes. Tetrakis(triphenylphosphine)palladium (0) (0.52 g, 0.45 mmol) was added and deoxygenation was continued for a further 10 minutes. The reaction was heated at 100° C. for 16 hours then allowed to cool and diluted with water (40 mL). The catalyst was removed by filtration through Hyflo® and the filtrate was extracted with EtOAc (×3). The combined extracts were washed with water then brine, dried (MgSO$_4$), filtered and evaporated. The residue was purified by chromatography on silica, eluting with 10-40% EtOAc/hexane to give the product (1.52 g, 64%). (400 MHz $^1$H, δ-CDCl$_3$) 1.37 (2H, m), 1.87 (2H, m), 2.61 (2H, m), 2.89-3.09 (4H, m), 3.91 (3H, s), 6.58 (1H, s), 7.15-7.26 (3H, m), 7.44 (2H, m), 7.61 (1H, m), 7.71 (1H, m). MS (ES+) 361, MH$^+$.

Step 4

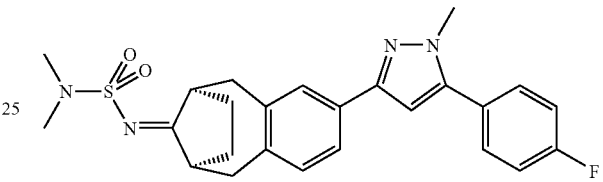

A solution of the ketone from Step 3 (0.360 g, 1.0 mmol), N,N-dimethylsulfamide (0.620 g, 5.0 mmol) and titanium (IV) ethoxide (tech., 0.63 mL, 3.0 mmol) in dry THF (5 mL) was stirred and heated at reflux under nitrogen for 16 hours. The reaction was allowed to cool to room temperature, poured into rapidly stirred brine (60 mL), stirred for 1 hour, then filtered through Hyflo®, washing with EtOAc. The layers of the filtrate were separated, and the aqueous layer was extracted with EtOAc. The combined organic extracts were washed with brine, dried (MgSO$_4$), filtered and evaporated. The residue was purified by chromatography on silica, eluting with 5-20% EtOAc/DCM, to give the imine (0.383 g, 82%). MS (ES+) 467, MH$^+$.

Step 5

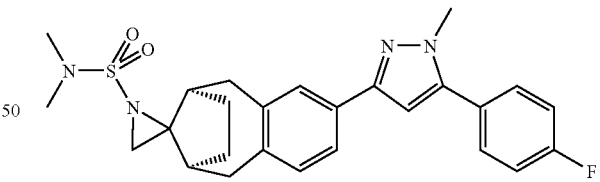

Sodium hydride (60% dispersion in oil, 0.223 g, 5.7 mmol) was added portionwise to a stirred suspension of trimethyl sulfoxonium iodide (1.261 g, 5.7 mmol) in dry DMSO (10 mL) at room temperature under nitrogen. After 1 hour at room temperature, a solution of the imine from Step 4 (1.783 g, 3.8 mmol) in dry DMSO (15 mL) was added such that the internal temperature remained below 30° C. The mixture was stirred at room temperature for 2 hours, then quenched with water (40 mL). The reaction was extracted with EtOAc and the combined organic extracts washed with water then brine, dried (MgSO$_4$), filtered and evaporated. The residue was purified by chromatography on silica, eluting with 20-50%

EtOAc/hexane, to give the aziridine (1.544 g, 84%). (360 MHz $^1$H, δ-CDCl$_3$) 1.30 (2H, m), 1.73 (2H, m), 2.24 (2H, m), 2.44 (2H, m), 2.80 (2H, m), 2.97 (6H, s), 3.59 (2H, m), 3.90 (3H, s), 6.56 (1H, s), 7.15 (3H, m), 7.43 (2H, m), 7.52 (1H, m), 7.58 (1H, m). MS (ES+) 481, MH$^+$.

Intermediate C

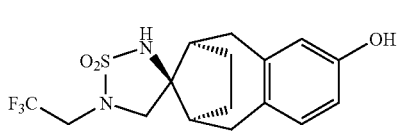

Prepared as described in WO 02/36555, Example 83, starting from homochiral 2-hydroxy-5,6,7,8,9,10-hexahydro-6,9-methanobenzo[a][8]annulen-11-one, obtained as described in Step 1 of the above Intermediate B preparation.

Intermediate D

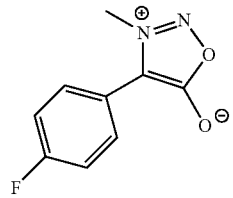

Step 1

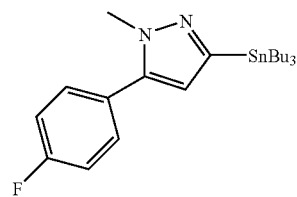

Methylamine (2.0M in methanol, 6 ml, 12 mmol) was added to a stirred solution of (±)-bromo(4-fluorophenyl)acetic acid (1.5 g, 6.4 mmol) in methanol (4 ml) at 0° C. The cooling bath was removed and the reaction was stirred at room temperature for 3 hours. The reaction mixture was evaporated and the residue was crystallised (methanol/water) to give the amino acid (795 mg, 67% in two batches) as a colourless solid. (400 MHz $^1$H, δ-D$_2$O) 2.61 (3H, s), 4.62 (1H, s), 7.24 (2H, t, J=8.8 Hz), 7.46-7.49 (2H, m).

Step 2

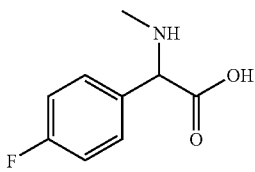

Sodium nitrite (250 mg, 3.6 mmol) was added portionwise to a stirred suspension of the amino acid from Step 1 (325 mg, 1.8 mmol) in water (1 ml) and concentrated hydrochloric acid (0.3 ml) at 0° C. After 1 hour diethylether (1 ml) was added, then after an additional 5 hours at 0° C., water (5 ml) was added and the mixture was extracted with dichloromethane (×4). The combined extracts were dried (Na$_2$SO$_4$), filtered and evaporated to give (±)-(4-fluorophenyl)(1-methyl-2-oxo-hydrazino)acetic acid (320 mg, 84%) as an oil. (400 MHz $^1$H, δ-CDCl$_3$, 1.5:1 mixture of isomers) 2.95 (1.8H, s), 3.59 (1.2H, s), 6.20 (0.4H, s), 6.71 (0.6H, s), 7.12-7.17 (2H, m), 7.28-7.31 (0.9H, m), 7.37-7.40 (1.1H, m), 8.3 (1H, br s).

Step 3

4-(4-fluorophenyl)-3-methyl-1,2,3-oxadiazol-3-ium-5-olate

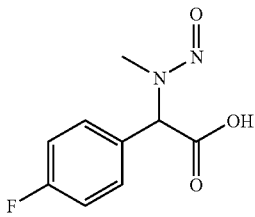

Trifluoroacetic anhydride (225 μl, 1.6 mmol) was added to a stirred solution of the product of Step 2 (320 mg, 1.5 mmol) in dry diethyl ether (15 ml) at 0° C. under nitrogen. After 3 hours the precipitate was collected by filtration to give the title compound (124 mg, 43%) as a colourless solid. A further sample (50 mg, 17%) was obtained by evaporation of the filtrate and purification of the residue by chromatography on silica, eluting with 1:1 ethyl acetate/hexanes. (360 MHz $^1$H, δ-CDCl$_3$) 4.12 (3H, s), 7.20 (2H, t, J=8.6 Hz), 7.55-7.59 (2H, m).

Step 4

5-(4-fluorophenyl)-1-methyl-3-(tributylstannyl)-1H-pyrazole

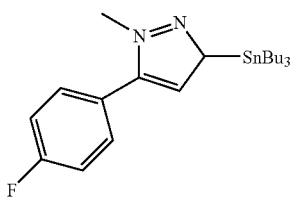

A solution of the product from Step 3 (120 mg, 0.62 mmol) and ethynyltributyltin (360 μl, 1.2 mmol) in m-xylene (750 μl) was heated at 140° C. under nitrogen for 36 hours. The reaction mixture diluted with toluene and loaded directly onto a silica column. Elution with 5 to 8% ethyl acetate/hexanes gave the title compound (63 mg, 22%) as an oil. (400 MHz $^1$H, δ-CDCl$_3$) 0.90 (9H, t, J=7.3 Hz), 1.08-1.12 (6H, m) 1.30-1.39 (6H, m), 1.56-1.61 (6H, m), 3.90 (3H, s), 6.33 (1H, s), 7.11-7.15 (2H, m), 7.36-7.40 (2H, m).

Example 1

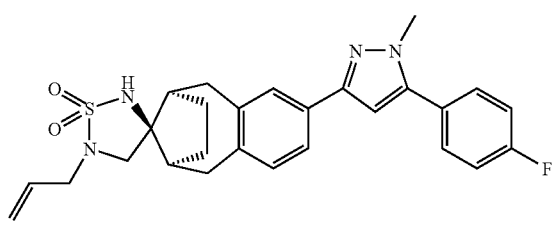

A solution of Intermediate B (96 mg, 0.2 mmol) and allylamine (114 mg, 2.0 mmol) in DMSO (2 mL) was stirred and heated at 100° C. in a sealed tube for 16 hours. After cooling, water (10 mL) was added, the reaction was extracted with EtOAc, and the combined organic extracts were washed with brine, dried (MgSO$_4$), filtered and evaporated. The residue was purified by chromatography on silica, eluting with 20-30% EtOAc/hexane, to give the title compound (82 mg, 84%). (360 MHz $^1$H, δ-CDCl$_3$) 1.35 (2H, m), 1.68 (2H, m), 2.42 (2H, m), 2.74 (2H, m), 3.19 (4H, m), 3.69 (2H, d, J=6.4 Hz), 3.90 (3H, s), 4.68 (1H, s), 5.28 (1H, d, J=10.3 Hz), 5.34 (1H, d, J=16.6 Hz), 5.90 (1H, m), 6.56 (1H, s), 7.15 (3H, m), 7.44 (2H, m), 7.52 (1H, m), 7.59 (1H, m). MS (ES+) 493, MH$^+$.

Examples 2-13

The compounds in table 1 were prepared from Intermediate B by the method of Example 1 substituting the appropriate amine for allylamine.

TABLE 1

| Example | R | m/z (M + H)$^+$ |
|---|---|---|
| 2 | nPr | 495 |
| 3 | neopentyl (CH$_2$C(CH$_3$)$_3$) | 523 |
| 4 | cyclobutylmethyl | 507 |
| 5 | Bn | 543 |
| 6 | nBu | 509 |
| 7 | cyclopropylmethyl | 507 |

TABLE 1-continued

| Example | R | m/z (M + H)$^+$ |
|---|---|---|
| 8 | CH$_2$CH$_2$CHF$_2$ | 549 |
| 9 | isobutyl | 495 |
| 10 | CH$_2$C(CH$_3$)$_3$ | 509 |
| 11 | CH$_2$CF$_2$CF$_3$ | 585 |
| 12 | CH$_2$CHF$_2$ | 517 |
| 13 | cyclopropyl | 493 |

Example 14

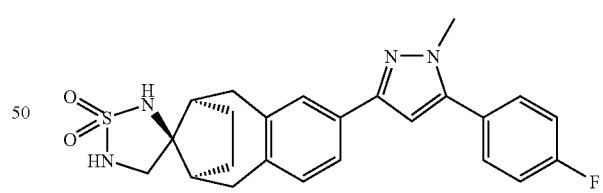

The procedure of Example 1 was repeated, substituting p-methoxybenzylamine for allylamine.

A solution of the resulting sulfamide (78 mg, 0.2 mmol) in TFA (2 mL) was stirred at room temperature for 3 hours. The reaction was concentrated in vacuo and saturated sodium bicarbonate solution (10 mL) was added. The mixture was extracted with DCM, the combined organic extracts were washed with brine, dried (MgSO$_4$), filtered and evaporated. The residue was purified by chromatography on silica, eluting with 40-60% EtOAc/hexane, to give the desired product. (49 mg, 80%). (360 MHz 1H, δ-CDCl$_3$) 1.37 (2H, m), 1.68 (2H, m), 2.42 (2H, m), 2.79 (2H, m), 3.24 (2H, m), 3.38 (2H, d, J=7.4 Hz), 3.90 (3H, s), 4.56 (1H, t, J=7.2 Hz), 4.60 (1H, s), 6.56 (1H, s), 7.16 (3H, m), 7.44 (2H, m), 7.53 (1H, m), 7.60 (1H, m). MS (ES+) 453, MH+.

Example 15

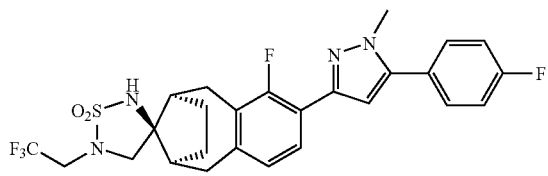

and

Example 16

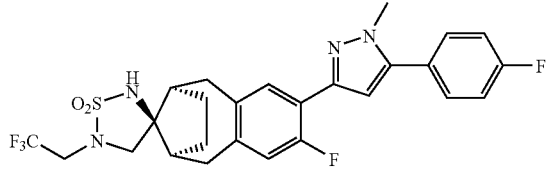

Step 1

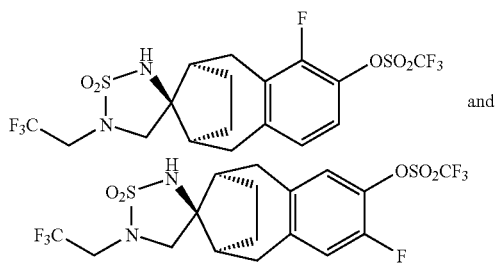

A mixture of Intermediate C (500 mg, 1.3 mmol) and N-fluoropyridinium triflate (500 mg, 2.0 mmol) in 1,2-dichloroethane (8 ml) was heated at reflux for 16 hours, then cooled to room temperature and concentrated in vacuo. The residue was diluted with water (30 ml) and extracted with dichloromethane (3×20 ml). The organics were dried (MgSO$_4$) and evaporated in vacuo to give a red foam (495 mg). The foam was purified by chromatography on SiO$_2$ [1% ethyl acetate/dichloromethane] to give the fluorophenols as a mixture of regioisomers (272 mg, 53%). M/Z ES$^-$ (393) (M-1)$^-$.

A solution of the isomeric fluorophenols (202 mg, 0.51 mmol) in pyridine (5 ml) at 0° C., under a nitrogen atmosphere, was treated with trifluoromethanesulfonic anhydride (170 μl, 1.0 mmol) and the mixture was stirred at 0° C. for 2 hours. The reaction was diluted with hydrochloric acid (1N, 30 ml) and extracted with ethyl acetate (2×40 ml). The organics were washed with brine, dried (MgSO$_4$) and evaporated in vacuo to a gummy foam (254 mg). The foam was purified by chromatography on SiO$_2$ [15% ethyl acetate/isohexane] to give the triflates as a mixture of regioisomers (173 mg, 65%). M/Z ES+(527) (MH)+.

Step 2

A mixture of the triflates from Step 1 (97 mg, 0.18 mmol), Intermediate D (86 mg, 0.18 mmol) and lithium chloride (23 mg, 0.54 mmol) in dioxane (2 ml) was degassed by a stream of nitrogen for 10 minutes. Tetrakis(triphenylphosphine)palladium(0) (23 mg, 0.02 mmol) was added and following a further 10 minutes of degassing the reaction was stirred at 100° C. for two and a half hours. After cooling to room temperature, more tetrakis(triphenylphosphine)palladium(0) (23 mg, 0.02 mmol) was added, the reaction was degassed for 10 minutes, then heated at 100° C. for 16 hours. The reaction was diluted with sodium bicarbonate (sat, 15 ml) and ethyl acetate (20 ml) and the mixture was filtered through a bed of Hyflo®. The phases were separated and the aqueous extracted with ethyl acetate (20 ml) The organics were washed with brine, dried (MgSO$_4$) and evaporated in vacuo to an orange/brown foam which was purified by chromatography on SiO$_2$ [ethyl acetate/isohexane 1:2] to give Example 12, less polar on SiO$_2$, as a white foam (23 mg, 23%) M/Z ES+(553) (MH)+ and Example 13, more polar on SiO$_2$, as a white foam (52 mg, 52%) M/Z ES+(553) (MH)+.

Example 17

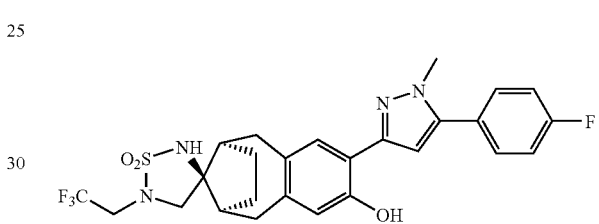

Step 1

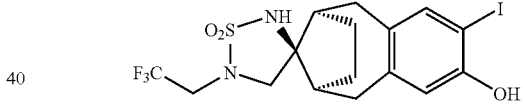

The enantiomer of Intermediate C was prepared by the same method as Intermediate C, starting with the first-eluted enantiomer obtained from the resolution described in Step 1 of the preparation of Intermediate B.

Aqueous sodium hypochlorite (4%, 25 g) was added dropwise to a cold (0° C.) solution of the enantiomer of Intermediate C (5.0 g, 13.3 mmol), sodium iodide (2.0 g, 13.3 mmol) and sodium hydroxide (532 mg, 13.3 mmol) in methanol (200 ml). The mixture was stirred at 0° C. for 2 hours, then treated with sodium thiosulfate (10% w/v, 200 ml), neutralised (1N HCl) and concentrated in vacuo. The residue was extracted with ethyl acetate (4×200 ml), and the organics washed with brine, dried (MgSO4) and evaporated in vacuo to a yellowish solid (7.25 g) which was purified by chromatography on SiO$_2$ [5% ethyl acetate/dichloromethane] to give the desired iodide as a white foam (5.4 g, 81%) M/Z ES$^-$ (501) (M-H)$^-$.

Step 2

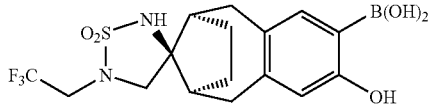

A mixture of iodophenol from Step 1 (502 mg, 1 mmol), pinacolborane (540 μl, 3.7 mmol) and triethylamine (0.45 ml, 3.2 mmol) in dioxane was degassed via a stream of nitrogen, [1,1'-bis(diphenylphosphino)ferrocene]-dichloropalladium (II) dichloromethane adduct (27 mg, 0.04 mmol) was added, and following a further period of degassing the reaction was heated at 80° C. for 16 hours. Further triethylamine (0.45 ml, 3.2 mmol), pinacolborane (540 Tl, 3.7 mmol) and Pd catalyst (27 mg, 0.04 mmol) were added, and following a period of degassing the reaction was heated at 80° C. for 24 hours. The reaction was cooled to room temperature, diluted with ethyl acetate (30 ml) and washed with HCl (1N, 3×15 ml). The organics were washed with brine, dried (MgSO$_4$) and evaporated in vacuo to a brown gum (640 mg) which was purified by filtration through a plug of silica and trituration with hot hexane to give a brown solid (345 mg, 69%) M/Z ES$^-$ (501) (M-1)$^-$.

Step 3

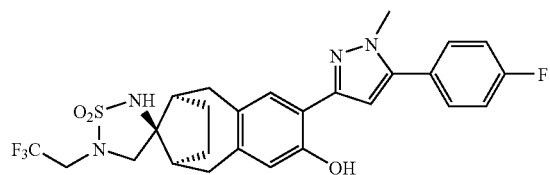

A mixture of the boronate from Step 2 (50 mg, 0.1 mmol), Intermediate A (32 mg, 0.1 mmol) and potassium phosphate (46 mg, 0.2 mmol) in DMF was degassed via a stream of nitrogen. Tetrakis(triphenylphosphine)palladium(0) (6 mg, 5.2 mmol) was added and following a further degassing the reaction was heated at 100° C., under microwave irradiation, for 10 minutes. The reaction was diluted with HCl (1N, 10 ml) and extracted with diethylether (2×30 ml). The organics were washed with water (2×30 ml) and brine, dried (MgSO$_4$) and evaporated in vacuo to a brown gum (84 mg) which was purified by column chromatography on silica [2% ethyl acetate/dichloromethane] to give a white solid (2.6 mg, 5%) M/Z ES$^-$ (551) (M-1)$^-$.

The invention claimed is:

1. A compound of formula I:

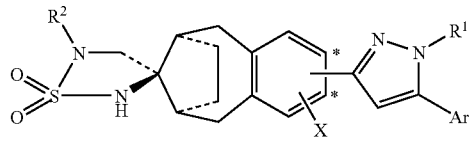

wherein the pyrazole group is attached at one of the positions indicated by an asterisk and X is attached at a position adjacent thereto;

X represents H, OH, C$_{1-4}$alkoxy, Cl or F;

Ar represents phenyl or 6-membered heteroaryl, either of which bears 0-3 substituents independently selected from halogen, CF$_3$, CHF$_2$, CH$_2$F, NO$_2$, CN, OCF$_3$, C$_{1-6}$alkyl and C$_{1-6}$alkoxy;

R$^1$ represents a hydrocarbon group of 1-5 carbon atoms which is optionally substituted with up to 3 halogen atoms; and R$^2$ represents H or a hydrocarbon group of 1-10 carbon atoms which is optionally substituted with up to 7 halogen atoms;

provided that when X is H, R$^2$ does not represent 2,2,2-trifluoroethyl; or a pharmaceutically acceptable salt thereof.

2. A compound according to claim 1 of formula IIa:

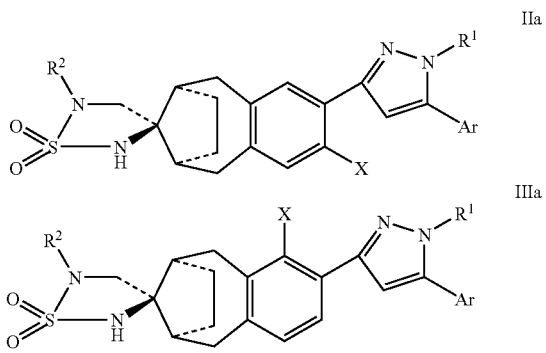

or formula IIIa:
or a pharmaceutically acceptable salt thereof.

3. A compound according to claim 1 wherein Ar represents phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro.

4. A compound according to claim 1 wherein R$^2$ represents H, benzyl, or alkyl, alkenyl, cycloalkyl or cycloalkylalkyl of up to 6 carbon atoms, or benzyl, and optionally bears up to 5 fluorine substituents.

5. A compound according to claim 2 wherein X is H, R$^1$ is methyl, Ar is 4-fluorophenyl and R$^2$ is selected from H, benzyl, n-propyl, 2,2-dimethylpropyl, n-butyl, isopropyl, t-butyl, 2,2,2-trifluoroethyl, 2,2-difluoroethyl, 2,2,3,3,3-pentafluoropropyl, 3,3,3-trifluoropropyl, allyl, cyclopropyl, cyclobutyl and cyclopropylmethyl. pg,29

6. The compound of formula:

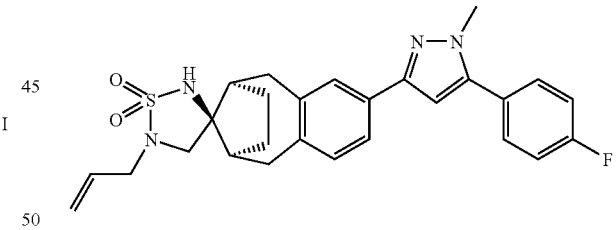

or a pharmaceutically acceptable salt thereof.

7. A pharmaceutical composition comprising a compound according to claim 1 and a pharmaceutically acceptable carrier.

8. A process for preparing a compound according to claim 1 in which R$^2$ is other than H comprising reaction of a compound of formula (1):

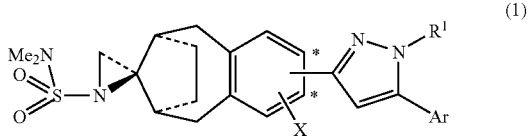

with $R^{2a}NH_2$;
where the pyrazole group is attached at one of the positions indicated by an asterisk and X is attached at a position adjacent thereto;

$R^{2a}$ is $R^2$ that is other than H;
and X and Ar, $R^1$ and $R^2$ are as defined in claim 1.

* * * * *

UNITED STATES PATENT AND TRADEMARK OFFICE
CERTIFICATE OF CORRECTION

PATENT NO. : 7,427,621 B2
APPLICATION NO. : 10/533272
DATED : September 23, 2008
INVENTOR(S) : Ian James Collins et al.

It is certified that error appears in the above-identified patent and that said Letters Patent is hereby corrected as shown below:

At column 8, formula (9) should be deleted and replaced with the following structure:

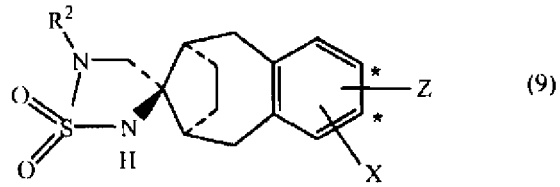

At column 20, line 39, delete "pg, 29".

Signed and Sealed this

Sixth Day of July, 2010

David J. Kappos
*Director of the United States Patent and Trademark Office*